United States Patent
Sternberger et al.

(10) Patent No.: US 6,837,121 B2
(45) Date of Patent: Jan. 4, 2005

(54) SAMPLING INTERFACE FOR A VEHICLE

(75) Inventors: Waynle I. Sternberger, Highland, MD (US); Stuart A. Goemmer, Bel Air, MD (US); Alexander E. Dence, Panama City, FL (US); Stanley G. Reach, Panama City, FL (US); Cheryl S. Schein, Frederick, MD (US); Micah A. Carlson, Baltimore, MD (US); William R. Allmon, Yardley, PA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/419,525

(22) Filed: Apr. 21, 2003

(65) Prior Publication Data

US 2004/0035191 A1 Feb. 26, 2004

Related U.S. Application Data

(60) Provisional application No. 60/375,340, filed on Apr. 24, 2002.

(51) Int. Cl.⁷ .................................................. G01N 1/04
(52) U.S. Cl. ............................... 73/864.71; 73/864.61; 73/864.63; 73/864.34
(58) Field of Search ........................ 73/864.71, 864.33, 73/864.31, 864.51, 864.61, 864.63, 864.73, 864.34

(56) References Cited

U.S. PATENT DOCUMENTS

| | | | |
|---|---|---|---|
| 1,925,592 A | * 9/1933 | Kleucker | ..................... 222/429 |
| 3,838,719 A | 10/1974 | Lederer | |
| 4,022,059 A | 5/1977 | Schontzler et al. | |
| 4,591,115 A | * 5/1986 | DeCarlo | ................. 244/135 C |
| 5,091,863 A | 2/1992 | Hungerford et al. | |
| 5,441,071 A | 8/1995 | Doherty et al. | |
| 5,560,825 A | * 10/1996 | Shafer | ........................ 210/430 |
| 5,922,943 A | * 7/1999 | Chapman, IV | ............... 73/40.7 |
| 6,230,551 B1 | * 5/2001 | Burniston | .................. 73/61.73 |
| 6,330,834 B1 | * 12/2001 | Weitzman | ................ 73/863.71 |

* cited by examiner

Primary Examiner—Michael Cygan
(74) Attorney, Agent, or Firm—Albert J. Fasulo, II

(57) ABSTRACT

The invention comprises a material sampling interface that includes one or more inlet manifolds and one or more outlet manifolds and piping running to and from the manifolds. There are rungs connecting the inlet manifold to the outlet manifold. In addition, a bypass rung is positioned between the inlet manifold and the outlet manifold, with a bypass valve positioned on the bypass. Each of the rungs has piping connected to the inlet and outlet manifolds and a removable reservoir connected to the piping. The reservoir includes an internal removable sampler adapted to sample the material. There is an inlet valve connected to the piping between the reservoir and the inlet manifold and an outlet valve connected to the piping between the reservoir and the outlet manifold. The invention is capable of sampling any flowable material including fluids, gases, particles, etc.

6 Claims, 2 Drawing Sheets

SAMPLING INTERFACE FOR A VEHICLE

CROSS-REFERENCE TO A RELATED APPLICATION

This application claims the benefit of U.S. Provisional application No. 60/375,340, filed Apr. 24, 2002, which is hereby incorporated by reference in its entirety.

STATEMENT OF GOVERNMENTAL INTEREST

This invention was made with government support under contract number N00024-98-D-8124 awarded by the Department of the Navy. The government has certain rights in this invention.

BACKGROUND OF THE INVENTION

1. Field of the Invention

This invention generally relates to a device for performing remote sampling and more particularly to an interface to be utilized with a submerged water-borne vehicle. The interface maintains fluid samples obtained in remote locations within removable reservoirs.

2. Description of Related Art

Unmanned vehicles are often used to perform activities that are difficult, dangerous, or impossible for humans to perform. One area where unmanned vehicles find success is in obtaining material samples that need to be chemically analyzed. For example, it is desirable to obtain chemical analysis of water samples at different locations and different depths. However, if there are high radiation or toxin levels, the water may be hazardous for humans to obtain the samples directly. Similarly, it may be impossible for humans to descend below certain water depths, while unmanned vehicles can exceed human limits.

Therefore, there have been attempts in the past to create devices that can obtain different fluid samples from different marine locations. However, these conventional devices merely collect samples without performing any analysis (or sampling) of the samples. Therefore, the samples must be transported to a separate location where they can be properly sampled and analyzed. However, during transport the samples can undergo unchanges. Therefore, such conventional systems may not accurately detect the true chemical nature of the marine region being sampled.

In addition, once the samples are returned to the testing facility, somewhat elaborate procedures must be performed in order to perform the chemical analysis. For example, in one chemical analysis system, a very delicate solid phase coated fiber must be submerged into the sample that was collected. The solid phase coated fiber must be exposed to the sample for an extended period of time in order to allow the solid phase coated fiber to absorb the various chemicals within the sample. Then, the solid phase coated fiber is inserted into a chemical analyzer which detects the chemicals absorbed by the solid phase coated fiber. Not only is this process time consuming, if the sample is not fairly fresh, the solid phase coated fiber may not be able to accurately absorb all the chemicals that were in the original sample, or may not be able to accurately show the chemical concentrations that were contained in the original sample. This is because chemicals may evaporate quickly upon opening the container or chemicals may change state by reacting with other chemicals within the sample during the transportation process.

The nature of the samplers enables both point samples and integrated samples. The integrated samples are ones where the sampling medium is run through the samplers for longer periods of time. This enables temporal averaging if the vehicle stays in one location or spatial averaging if the vehicle is in motion.

In view of the forgoing, the following invention has been devised to provide an efficient way to quickly and accurately perform remote sampling and analysis. In addition, the invention described below can be used in any environment where material can be pumped into the sampling interface, including gas, liquid, and particle environments.

SUMMARY OF THE INVENTION

As explained in greater detail below, the invention comprises a material sampling interface that includes one or more inlet manifolds, one or more outlet manifolds and piping running to and from the manifolds. There are rungs connecting the inlet manifold to the outlet manifold. In addition, a bypass rung is positioned between the inlet manifold and the outlet manifold, with a bypass valve positioned on the bypass.

Each of the rungs has piping connected to the inlet and outlet manifolds and a removable reservoir connected to the piping. The reservoir includes an internal removable sampler adapted to sample the material. There is an inlet valve connected to the piping between the reservoir and the inlet manifold and an outlet valve connected to the piping between the reservoir and the outlet manifold. The invention is capable of sampling any flowable material including fluids, gases, and particles.

A controller connected to the bypass valve and the inlet valve controls flushing of the inlet manifold and filling of the reservoirs. The controller can be a remotely operated controller or a programmable controller. The controller controls when material flows into and out of the reservoirs.

The invention includes at least one pump connected to the inlet manifold. The pump can be run at various flow rates. The pump pumps the material from outside the material sampling interface into the inlet manifold. In addition, a filter is connected to the inlet manifold. The filter prevents undesirable particles from contaminating the inlet manifold. The invention also utilizes a one-way valve for the outlet valve to prevent the material from passing from the outlet manifold back into the reservoir. The invention also includes sealing quick disconnects on the piping adjacent ends of the reservoir to allow the reservoir to be easily removed.

When using the invention, one first mounts a sampler within a reservoir and then mounts the reservoir within the material sampling interface. The reservoir is then filled with an inert substance such as deionized water. The material sampling interface is then transported to a first (possibly uninhabitable or other) location where material (e.g., the surrounding water or gas atmosphere) from outside the material sampling interface is pumped into the reservoir. The pumping process displaces the deionized water from the reservoir. After the reservoir is filled with sampling material, a valve is closed to retain the material within the reservoir. These operations are controlled by a remotely operated or pre-programmed controller.

The material sampling interface is then transported back to a location that is safe for humans, the reservoir is removed from the material sampling interface, and the sampler is removed from the reservoir. If necessary, after the reservoir is removed from the sampling interface (but before the sampler is removed from the reservoir) the reservoir can undergo additional agitation to increase material absorption within the sampler. After the sampler is removed from the reservoir, it is then placed into a chemical analyzer that analyzes the chemical properties of the material that was absorbed by the sampler.

The invention produces a number of advantages when compared to conventional systems. Specifically, the invention exposes the sampler (or analyzer) to the sample as the sample is being obtained. This allows the sampler (analyzer) to absorb chemicals from the sample while the sample is still fresh and in its naturally occurring state. This increases the likelihood that highly volatile chemicals (which may easily evaporate when the reservoir is opened) or chemicals that may easily combine with the bulk material (the water) will be collected by the sampler. To the contrary, conventional systems that have a large time lag between collection of the sample and insertion of the sampler into the sample, may lose the opportunity to absorb chemicals that exist in the sample only when the sample is fresh. Therefore, the sampler (analyzer) will maintain a more accurate representation of the sample than conventional systems that have a time lag between the time period when the sample is obtained and when the sampler (analyzer) is inserted into the material.

In addition, the invention exposes the sampler (analyzer) to the sample for an extended period of time (the time necessary to transport the material sampling interface back to the analysis lab) which allows the sampler (analyzer) to be fully exposed to the sample. Therefore, the sampler can be immediately analyzed as soon as the material sampling interface arrives at the analysis lab. Further, because the invention allows the reservoirs to be individually disconnected from the material sampling interface, the reservoirs can be transported separately from the material sampling interface. Thus, with the invention, the material sampling interface can be left in the field for an extended period of time with its reservoirs being periodically replaced and sent back to the analysis lab for analysis.

In addition, the bypass rungs can be used to flush common plumbing to preclude cross-contamination. Also, the general bypass can be used to flush the inlet crud filter.

DETAILED DESCRIPTION

Figure 1:
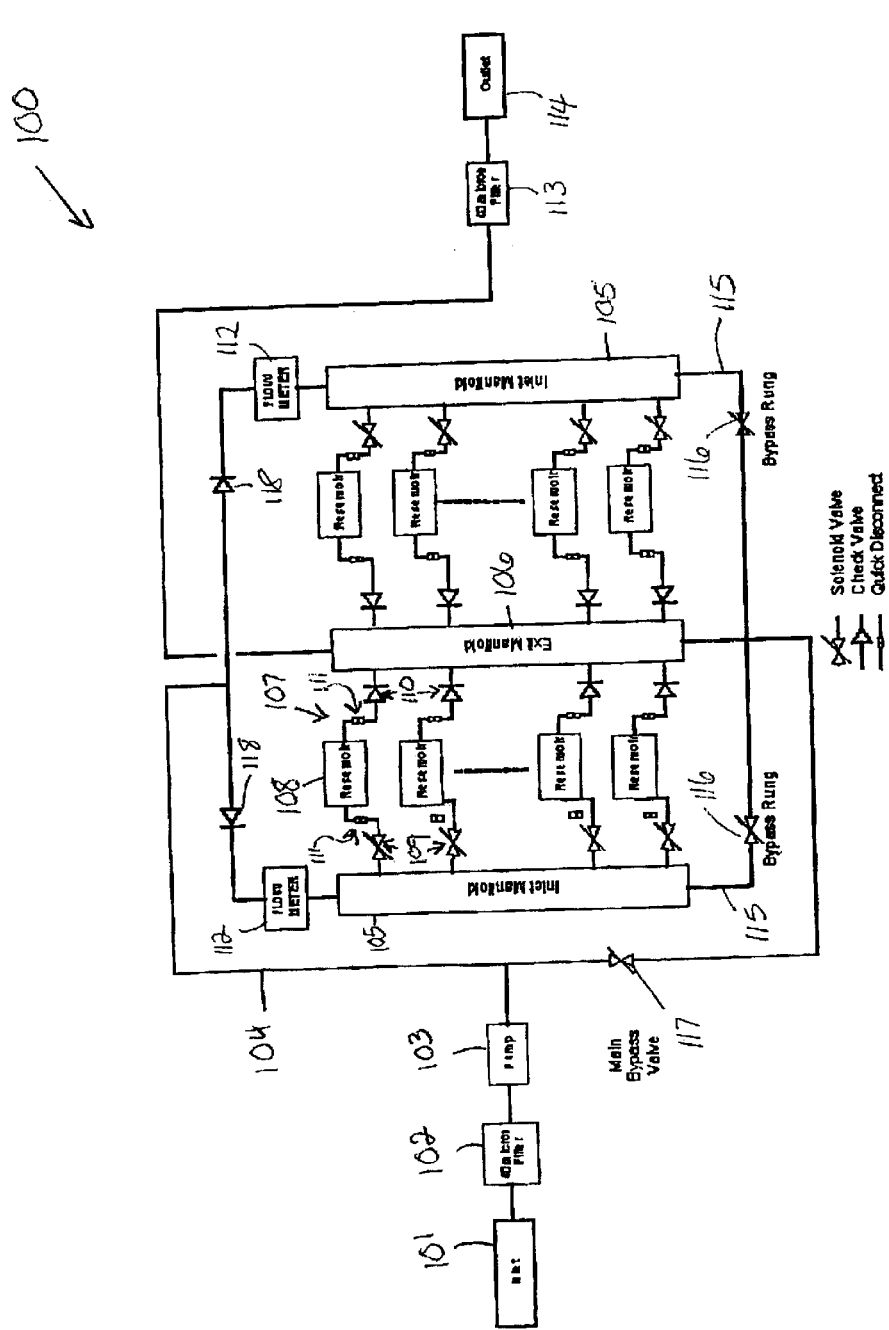
FIG. 1 is a schematic drawing illustrating one embodiment of the inventive material sampling interface.

As shown FIG. 1, the invention comprises a material sampling interface 100 that includes an inlet 101, a filter 102 (e.g., 40 micron) and a pump 103 which transfers material from outside the interface 100 to the piping 104 of the interface 100.

Figure 2:
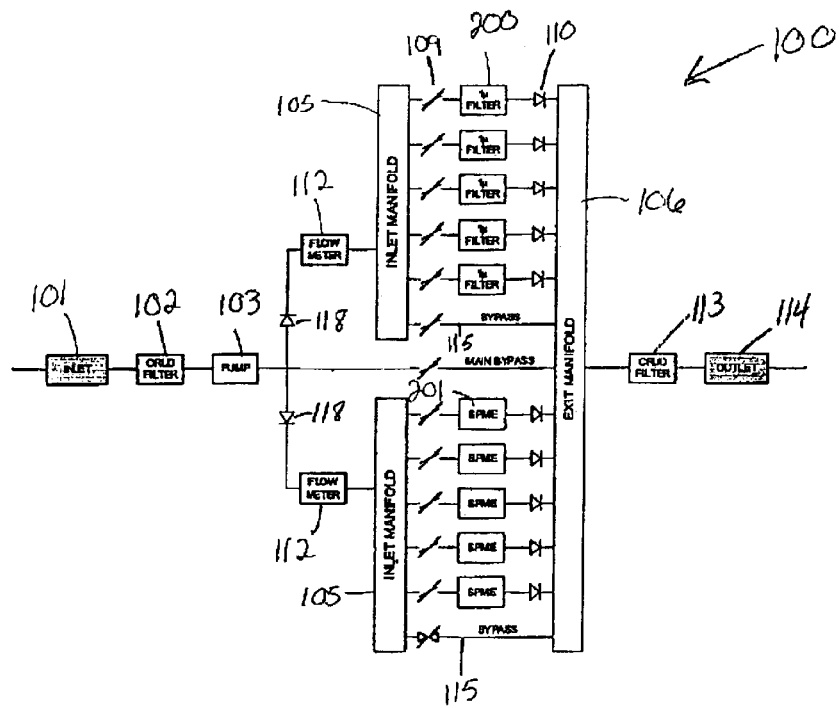
FIG. 2 is a schematic drawing illustrating another embodiment of the inventive material sampling interface.

The structure includes one or more inlet manifolds 105 and one or more outlet (exit) manifolds 106 and piping 104 running to and from the manifolds. While FIGS. 1 and 2 illustrate embodiments with two inlet manifolds 105 and one outlet manifold 106, the invention is not limited to any specific number of inlet or outlet manifolds. Instead, each specific application of the material sampling interface 100 and its restrictions and needs will control if and how many manifolds are required. Further, the invention does not require the use of manifolds and, instead, the manifolds are used in these examples as a matter of convenience and to reduce the amount of individual plumbing (piping).

There are rungs 107 connecting the inlet manifold 105 to the outlet manifold 106. In addition, a bypass rung 115 is positioned between the inlet manifold 105 and the outlet manifold 106, with a bypass valve 116 positioned on the bypass piping 115. When the bypass valve 116 opens, and valves to the individual reservoirs 108 are closed, the inlet manifold 105 can be flushed by running material directly through the inlet manifold 105 to the exit manifold 106 throughout the bypass 115.

Each of the rungs 107 has piping connected to the inlet and outlet manifolds 105, 106 and a removable reservoir 108 connected to the piping. The reservoir 108 can simply be a material container or can include any form of sampler or analyzer internally that can sample/analyze the material within the reservoir 108, as the material is being collected within the reservoir 108. FIG. 2, discussed in greater detail below, illustrates some options for analyzers/samplers within the reservoir 108. There is an inlet valve 109 connected to the piping between the reservoir 108 and the inlet manifold 105 and an outlet valve 110 connected to the piping between the reservoir 108 and the outlet manifold 106. The inlet valve 109 is preferably the type of valve that can be controlled (such as a solenoid-type valve) while the outlet valve 110 is preferably a mechanical one-way valve. Alternatively, the outlet valve 110 could also be a controlled-type valve.

The invention includes at least one pump connected to the inlet manifold 105. The pump pumps the material from outside the material sampling interface into the inlet manifold 105. In addition, a filter is connected to the inlet manifold 105. The filter prevents particles from contaminating the inlet manifold 105. The invention also utilizes a one-way valve for the outlet valve to prevent the material from passing from the outlet manifold 106 back into the reservoir 108. The invention also includes self-sealing quick disconnects on the piping adjacent ends of the reservoir 108 to allow the reservoir 108 to be easily removed.

Material flows from the outlet manifold 106 through piping to an outlet 114. The pump 103 can be reversed to clear out the filter 102 when necessary. In such a situation, in order to avoid drawing in contaminants that may enter through the outlet 114, the invention can also include a second filter 113 similar to filter 102. The invention is capable of sampling any flowable material including fluids, gases, particles, etc.

Flowmeters 112 can be included to measure flow rates and flow volumes of the material that passes through the inlet manifold 105. Such information allows the controller to calculate when enough material has passed through the inlet manifold 105 and surrounding piping to ensure that a specific reservoir 108 has been filled with enough sample material to provide accurate sampling. The invention includes one-way valves to prevent inappropriate backflow of material that could damage the flowmeters.

Quick disconnects 111 allow each of the reservoirs 108 to be quickly and easily removed from the interface 100. The sealing quick disconnects 111 can be any type of piping disconnect devices that prevent material flow when the parts are separated and allow material flow when the parts are connected. This feature allows reservoirs 108 to be easily removed from the interface without disturbing the material within the reservoir. Further, such a structure allows reservoirs to be removed and transported to an analyzing facility without having to transport the entire interface to the analyzing facility.

FIG. 2 illustrates another embodiment and includes many of the same devices mentioned with respect to FIG. 1, above.

The same devices are identified using the same numbers and a redundant discussion of the same as avoided. One aspect of the structure shown in FIG. 2 that is different from the structure shown in FIG. 1 is that the inlet manifolds 105 are placed on opposite sides of the exit manifold in FIG. 1, while the inlet manifolds 105 are placed on the same side of the exit manifold 106 in the structure in FIG. 2. As mentioned above, the invention is not limited to any specific embodiment shown in the Figures. To the contrary, there are a number of different arrangements that could be utilized with the invention, depending upon the space available for the interface, the type of material the interface will be sampling, and other requirements. Thus, while in some examples herein there are two (or more) inlet manifolds on either side of the outlet manifold. However, this is just a packaging convenience and has no bearing on the functionality or intended purpose of the invention.

In addition, each of the reservoirs 200, 201 shown in FIG. 2 illustrates different types of sampling/collection devices. The reservoirs 200 comprise filters while the reservoirs 201 have internal samplers (e.g., solid phase micro-extraction (SPME) fibers). The reservoirs could also include internal analyzers.

The filter reservoirs 200 are useful for preserving various particulates which could occur in a material sample. The size of the openings in the filter-type reservoirs 200 can be selected to match the specific type of material particulates expected to be encountered. The internal sampler-type reservoirs 201 include sampling devices that are designed to absorb and retain various chemical residue from the sample. The samplers are removed from the reservoirs 201 and inserted into a chemical analyzer to provide a listing and distribution of different chemicals that were collected by the reservoir 201.

With the sampler-type reservoirs 201, the user initially mounts a sampler within the reservoir 201, and then mounts the reservoir 201 within the material sampling interface. The reservoir 201 can be filled with an inert substance such as deionized water. The material sampling interface is then transported to a first (possibly inhabitable or dangerous) location where material from outside the vehicle is pumped into the reservoir 201. The pumping process displaces the deionized water from the reservoir 201. After the reservoir 201 is filled with material, a valve is closed to retain the material within the reservoir 201. These operations are controlled by a remotely operated or pre-programmed controller.

The material sampling interface is then transported back to a location that is safe for humans, the reservoir 201 is removed from the material sampling interface and the sampler is removed from the reservoir 201. If necessary, after the reservoir 201 is removed from the sampling interface (but before the sampler is removed from the reservoir 201) the reservoir 201 can undergo additional agitation to increase material absorption within the sampler or placed in cold storage to be analyzed later. After the sampler is removed from the reservoir 201, it is then placed into a chemical analyzer that analyzes the chemical properties of the material that was absorbed by the sampler.

Figure 3:
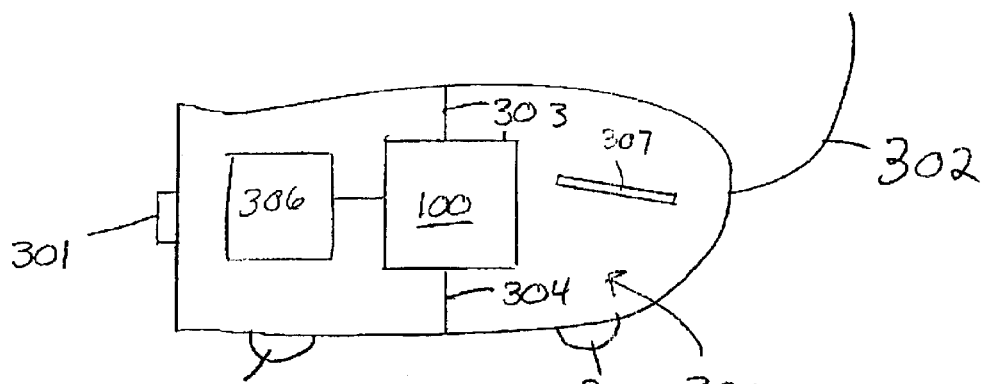
FIG. 3 is a schematic drawing of the inventive material sampling interface within a vehicle.

FIG. 3 illustrates a vehicle 300 used to transport the interface 100. The vehicle includes inlet 303 and outlet 304 piping (and associated through-hull connections) to allow material outside the vehicle to be collected by the interface 100. Depending upon the type and location of material being sampled, the vehicle can include one or more of the features shown in FIG. 3.

The interface 100 can sample any flowable material, including liquids, gases, solid particles, etc. Therefore, the vehicle 300 can be configured to travel on land, on water, under water, underground, in the air, in outer space, etc. Thus, FIG. 3 illustrates that the vehicle had an aero dynamic or hydrodynamic outer shape. Depending upon application, the vehicle 300 can include wheels 305 (or other similar ground transportation contact points such as tracks, etc.) wings, aerofoils, water foils, etc. 307. Further, the vehicle 300 can comprise a lighter-than-air vehicle (e.g., Zeppelin).

In addition, the vehicle can be towed or tethered behind, below, above, in front of etc., a tow vehicle, or the vehicle 300 can be self-propelled in any of the forgoing environments. The vehicle 300 can be remotely controlled through a wired or wireless connection or can be programmed to operate autonomously. Therefore, a tether or wired connection 302 is shown in FIG. 3. In addition, item 302 could represent an antenna.

Item 306 illustrates a controller that could include a memory and central processing unit. The details of the controller 306 are not considered novel aspects of this invention, however the use of a controller is. The controller 306 preferably includes connections to all the devices shown in FIGS. 1 and 2. These detailed wiring connections to and from the controller 306 are not illustrated so as not to obscure the piping and other features shown in FIGS. 1 and 2. The wiring connections are considered rudimentary and would be easily known by one ordinarily skilled in the art. For example, the controller 306 could be connected to the pump 103, flowmeters 112, valves 109, 117, 116, etc. In one embodiment, internal analyzers within the reservoirs 108 provide an immediate chemical analysis of the material collected by the reservoir. The analyzers could be connected directly to the controller 306 so that the data from the analyzers could be output to and stored in the controller in real time as the material is being collected in the reservoir. Such data could similarly be transmitted through the antenna 302 to a remote data collector in real time.

The controller controls when material flows into and out of the reservoirs 108 by coordinating the activation of the pump 103 with the opening of various valves, 109, 116, 117, etc. In addition, the controller 306 can act on information from the flowmeters 112 to determine when a sufficient volume of material has passed through the inlet manifold 105 to fill the appropriate reservoirs 108, even considering the material volume of the intervening piping. In addition, if the flow meter 112 shows a reduced volume of flow compared to the pump action, the controller 306 can sense that the filter 102 is clogged. In such a situation, the controller 306 could initiate a backflow sequence that would open the bypass valves and reverse the pump 103 to allow the filter 102 to be flushed output.

As mentioned above, the controller 306 can respond to input from a remote-control, or the controller 306 can be pre-programmed to act autonomously. To aid in autonomous operation, the controller can include positioning devices such as a global positioning system (GPS) locators. In addition, the propulsion device 301 (which can comprise a water or air propeller, rocket, internal combustion engine, electrical motor, nuclear powered device, solar powered device, etc.) is controlled by the controller 306 to determine the speed at which the vehicle 300 travels. The vehicle can also include various optical sensors (sonar, radar, etc.) to guide its movements around obstacles.

The invention produces a number of advantages when compared to conventional systems. More specifically, the invention exposes the sampler (or analyzer) to the sample as the sample is being obtained. This allows the sampler (analyzer) to absorb chemicals from the sample while the sample is still fresh and in its naturally occurring state. This increases the likelihood that highly volatile chemicals (which may easily evaporate when the reservoir is opened) or chemicals that may easily combine with the bulk material (the water) will be collected by the sampler (analyzer). To the contrary, conventional systems that have a large time lag between collection of the sample and insertion of the sampler into the sample may lose the opportunity to absorb chemicals that exist in the sample only when the sample is fresh. Therefore, the sampler (analyzer) will maintain a more accurate representation of the sample then conventional systems that have a time lag between the time period when the sample is obtained and when the sampler is inserted into the material.

In addition, the invention exposes the sampler (analyzer) to the sample for an extended period of time (the time necessary to transport the material sampling interface back to the analysis lab) which allows the sampler (analyzer) to be fully exposed to the sample. Therefore, the sample can be immediately analyzed as soon as the material sampling interface arrives at the analysis lab. Further, because the invention allows the reservoirs to be individually disconnected from the material sampling interface, the reservoirs can be transported separately from the material sampling interface or stored in cold storage. Thus, with the invention, the material sampling interface can be left in the field for an extended period of time with its reservoirs being periodically replaced and sent back to the analysis lab for analysis.

We claim:

1. A material sampling interface comprising:
   at least one inlet manifold;
   at least one pump connected to said inlet manifold, said pump being adapted to pump said material into said inlet manifold;
   at least one outlet manifold;
   a plurality of rungs positioned between said inlet manifold and said outlet manifold;
   a bypass positioned between said inlet manifold and said outlet manifold; and
   a controller connected to said pump, said rungs and said bypass,
   wherein each of said rungs includes a reservoir and a plurality of valves,
   wherein said reservoir includes a sampler inside said reservoir adapted to sample said material,
   wherein an inlet valve is positioned between each reservoir and said inlet manifold and an outlet valve is positioned between each reservoir and said outlet manifold, and
   wherein said controller controls said pump, said inlet valve, said outlet value, and said bypass to cause material to flow into and out of said reservoir to allow said sampler to sample said pumped material.

2. The interface in claim 1, wherein said material comprises one of a fluid, a gas, and particles.

3. The interface in claim 1, wherein said controller comprises one of a remotely operated controller and a programmable controller.

4. The interface in claim 1, further comprising at least one filter connected to said inlet manifold, said filter being adapted to prevent particles from contaminating said inlet manifold.

5. The interface in claim 1, wherein said outlet valve comprises a one-way valve adapted to prevent said material from passing from said outlet manifold to said reservoir.

6. The interface in claim 1, wherein each of said rungs includes sealing quick disconnects adjacent ends of said reservoir.

* * * * *